(12) United States Patent
Bewick-Sonntag et al.

(10) Patent No.: US 8,969,652 B2
(45) Date of Patent: Mar. 3, 2015

(54) DISPOSABLE ABSORBENT ARTICLE

(75) Inventors: Christopher Philip Bewick-Sonntag, Cincinnati, OH (US); Ronald Dean Cramer, Cincinnati, OH (US); James A. Hatton, Liberty, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 568 days.

(21) Appl. No.: 13/235,870

(22) Filed: Sep. 19, 2011

(65) Prior Publication Data

US 2012/0071847 A1    Mar. 22, 2012

Related U.S. Application Data

(60) Provisional application No. 61/385,130, filed on Sep. 21, 2010.

(51) Int. Cl.
| | | |
|---|---|---|
| *A61F 13/15* | (2006.01) | |
| *A61F 13/511* | (2006.01) | |
| *A61F 13/537* | (2006.01) | |
| *A61F 13/53* | (2006.01) | |
| *A61F 13/47* | (2006.01) | |

(52) U.S. Cl.
CPC ... *A61F 13/51121* (2013.01); *A61F 2013/5307* (2013.01); *A61F 2013/4708* (2013.01); *A61F 13/537* (2013.01); *A61F 13/5116* (2013.01)
USPC ............................ 604/378; 604/368; 604/374

(58) Field of Classification Search
CPC ........... A61F 13/537; A61F 2013/4708; A61F 2013/5307
USPC .................................. 604/368, 374–376, 378
See application file for complete search history.

(56) References Cited

U.S. PATENT DOCUMENTS

| | | |
|---|---|---|
| 3,890,974 A | 6/1975 | Kozak |
| 3,929,135 A | 12/1975 | Thompson |
| 4,076,663 A | 2/1978 | Masuda et al. |
| 4,157,724 A | 6/1979 | Persson |
| 4,264,289 A | 4/1981 | Day |
| 4,278,113 A | 7/1981 | Persson |
| 4,321,924 A | 3/1982 | Ahr |

(Continued)

FOREIGN PATENT DOCUMENTS

| | | |
|---|---|---|
| EP | 1627618 | 2/2006 |
| WO | WO 92/18171 | 10/1992 |
| WO | WO 00/59438 | 12/2000 |

OTHER PUBLICATIONS

International Search Report dated Jan. 23, 2012, PCT/US2011/052535, 11 pages.

*Primary Examiner* — Lynne Anderson
(74) *Attorney, Agent, or Firm* — Andres E. Velarde; Amanda T. Barry

(57) ABSTRACT

A sanitary napkin is disclosed as a form of disposable absorbent article. It has an absorbent core and a hydrophobic topsheet that has an upper side that is to be worn against a user's body. The topsheet is selected from a group of nonwoven topsheets and apertured film topsheets. A trace amount of a fibrous superabsorbent material, in the range of 0.30 and 3.5 grams of superabsorbent material per square meter, is provided in a fibrous matrix in a secondary topsheet that is in intimate contact with the lower side of the topsheet. The fibrous matrix is made by airlaying the superabsorbent material with cellulose and bi-component fiber onto a non-woven carrier.

3 Claims, 1 Drawing Sheet

(56) References Cited

U.S. PATENT DOCUMENTS

| | | | |
|---|---|---|---|
| 4,324,246 | A | 4/1982 | Mullane et al. |
| 4,342,314 | A | 8/1982 | Radel et al. |
| 4,352,649 | A | 10/1982 | Jacobsen et al. |
| 4,353,686 | A | 10/1982 | Hosler et al. |
| 4,425,130 | A | 1/1984 | DesMarais |
| 4,463,045 | A | 7/1984 | Ahr et al. |
| 4,494,278 | A | 1/1985 | Kroyer et al. |
| 4,589,876 | A | 5/1986 | Van Tilburg |
| 4,609,518 | A | 9/1986 | Curro et al. |
| 4,627,806 | A | 12/1986 | Johnson |
| 4,629,643 | A | 12/1986 | Curro et al. |
| 4,640,810 | A | 2/1987 | Laursen et al. |
| 4,650,409 | A | 3/1987 | Nistri et al. |
| 4,654,039 | A | 3/1987 | Brandt et al. |
| 4,724,980 | A | 2/1988 | Farley |
| 4,950,264 | A | 8/1990 | Osborn |
| 5,006,394 | A | 4/1991 | Baird |
| 5,009,653 | A | 4/1991 | Osborn |
| 5,102,597 | A | 4/1992 | Roe et al. |
| H1298 | H | 4/1994 | Ahr et al. |
| 5,425,725 | A * | 6/1995 | Tanzer et al. ............ 604/368 |
| 5,718,698 | A | 2/1998 | Dobrin et al. |
| 5,968,026 | A * | 10/1999 | Osborn et al. ............ 604/378 |
| 6,837,956 | B2 * | 1/2005 | Cowell et al. ............ 156/252 |
| 7,172,801 | B2 | 2/2007 | Hoying et al. |
| 7,270,861 | B2 | 9/2007 | Broering et al. |
| 7,410,683 | B2 | 8/2008 | Curro et al. |
| 7,507,459 | B2 | 3/2009 | Turner et al. |
| 7,553,532 | B2 | 6/2009 | Turner et al. |
| 7,648,752 | B2 | 1/2010 | Hoying et al. |
| 7,670,665 | B2 | 3/2010 | Hoying et al. |
| 7,682,686 | B2 | 3/2010 | Curro et al. |
| 7,718,243 | B2 | 5/2010 | Curro et al. |
| 7,732,657 | B2 | 6/2010 | Hammons et al. |
| 7,838,099 | B2 | 11/2010 | Curro et al. |
| 2004/0024377 | A1 * | 2/2004 | Karami ............ 604/385.24 |
| 2007/0270070 | A1 * | 11/2007 | Hamed ............ 442/414 |
| 2009/0030390 | A1 | 1/2009 | Hammons et al. |
| 2009/0030391 | A1 | 1/2009 | Hammons et al. |
| 2010/0048072 | A1 * | 2/2010 | Kauschke et al. ............ 442/1 |

\* cited by examiner

DISPOSABLE ABSORBENT ARTICLE

CROSS REFERENCE TO RELATED APPLICATION

This application claims the benefit of U.S. Provisional Application No. 61/385,130 filed Sep. 21, 2010.

FIELD OF THE INVENTION

This disclosure relates to disposable absorbent articles such as feminine hygiene products that have an absorbent core covered by a topsheet.

BACKGROUND OF THE INVENTION

Disposable absorbent articles such as feminine hygiene products are designed to absorb fluids from the wearer's body, and are well known in the art. Users of feminine hygiene products have several concerns. Leakage from products like catamenial pads, and in particular sanitary napkins, is a significant concern. The feel of the product against the wearer's body is also a concern. Users of such products want the surface of such products to provide a cleaner, more sanitary and drier aspect than common cloth or hydrophilic nonwoven materials have historically provided.

To provide better comfort, current sanitary napkin products are typically provided with a topsheet that is flexible, soft feeling, and non-irritating to the wearer's skin. The topsheet does not itself hold the discharged fluid. Instead, the topsheet is fluid-permeable to allow the fluids to flow into an absorbent core.

Over the years, topsheets have improved to provide a cleaner, drier, and more comfortable in-use experience. In some feminine hygiene products, the topsheet is made of a hydrophobic material. These materials can include phobic nonwovens, hi-loft nonwovens, and softer films with significant texture (micro apertures, nubs that can trap fluid within the film structure etc), and can be manufactured from a wide range of materials such as apertured plastic films, natural fibers (e.g., wood or cotton fibers), synthetic fibers (e.g., polyester or polypropylene fibers) or from a combination of natural and synthetic fibers. The hydrophobic nature of these materials helps to isolate the wearer's skin from liquids absorbed by the product and thus improves comfort by reducing the phenomenon known as "rewet".

Absorbent cores are well known in the art, and have conventionally included tangled masses of fibers, i.e., fibrous webs that can imbibe fluids both by an absorption mechanism (in which fluid is taken up by the fiber material itself) and by a wicking mechanism (in which fluid is acquired by, distributed through, and stored in capillary interstices between fibers).

One way to improve the absorbent capacity of an absorbent core is to add a superabsorbent material, such as a polymeric gelling material (also referred to as hydrogel-forming material, superabsorbent polymers, etc.) that imbibes fluid, forming a gel that retains the fluid. The superabsorbent material can be provided in particulate form, and encased or enveloped within a tissue layer. Such encased or enveloped cores are often referred to as tissue laminate cores. See, for example, U.S. Pat. No. 4,950,264 (Osborn), issued Aug. 21, 1990 and U.S. Pat. No. 5,009,653 (Osborn), issued Apr. 23, 1991, which disclose tissue laminate cores used in sanitary napkin products.

While superabsorbent materials are quite good at absorbing urine and similar water-based fluids, they absorb blood-based fluids much more slowly (they absorb urine 10 to 12 times faster than they absorb blood-based fluids). Because cellulose fluff—a common core material—absorbs blood-based fluids much more quickly than conventional superabsorbent materials do, relatively high levels of superabsorbent material are needed to provide significant improvements in the rewet, dryness, and absorbing capacity of feminine hygiene products. Conventionally, the concentration of superabsorbent materials in the core of a feminine hygiene product is in the range of 5-200 grams per square meter of material.

At this concentration, larger superabsorbent material particles can act to create a rough, sandpaper-like texture. This effect can reduce the user's comfort, particularly in thin ultra type sanitary pads and pantiliners. In addition, swollen superabsorbent material particles can hinder the fluid movement within an absorbent core by filling the voids in the fiber matrix, thereby restricting permeability of the fiber matrix. When this occurs near the topsheet, it can impair fluid transport to other parts of the product, effectively reducing the capacity of the product and reducing its effectiveness. Accordingly, superabsorbent materials are conventionally moved away from the topsheet in a feminine hygiene product, sometimes being added only or primarily to layers of the core near the backsheet.

Although the properties of a phobic nonwoven topsheet helps to keep fluids in the core, the tendency of such topsheets to repel fluid creates a risk that the fluid will flow off the topsheet, rather than flow through the topsheet and into the absorbent core. This challenge is particularly keen in connection with feminine hygiene products, which commonly encounter fluid flow rates of less than 1-3 gram per hour, rather than the gushing flow rates commonly encountered by incontinence products. For such fluid to flow into a feminine hygiene product, it must overcome not only the hydrophobic properties of the topsheet, but also the natural adhesion of the fluid to bodily surfaces.

To address these concerns, steps are sometimes taken to make the upper surface of the topsheet hydrophilic. This has been done, for example, by treating the upper surface with a surfactant, as described in U.S. Pat. No. 4,950,254. However, treating the topsheet in this way may make it less comfortable against the user's skin.

To help ensure that fluids flow into the absorbent core, some feminine hygiene products with hydrophobic phobic topsheets are constructed with what is sometimes referred to as a secondary topsheet 20 directly beneath the topsheet. This secondary topsheet 20 is designed to acquire the fluid on a liquid-permeable topsheet and distribute it to the underlying absorbent core. To help ensure that the secondary topsheet transfers the fluid to the absorbent core, secondary topsheets are typically made from an air-laid-tissue web or a synthetic nonwoven that has sufficient capillarity to draw the fluid through the topsheet. To ensure that the fluid flow continues on to the absorbent core, the secondary topsheet is commonly designed with more permeability than the absorbent core, and less capillarity than the absorbent core.

While secondary topsheets help to increase the probability of fluid bridging across a hydrophobic topsheet, there remains a need for new and better ways to encourage liquid flow through a phobic nonwoven topsheet and into either an absorbent core or secondary topsheet.

Fluid transport has commonly been achieved by increasing the capillarity of the layer where the fluid is to be directed. This can be done in several ways. For example, densifying the layer where the fluid is to be directed decreases the average pore size in that layer, increasing capillarity of that layer with respect to an undensified layer. Alternatively, a blend of fine fibers and particles that have a high surface area can be added to the layer where the fluid is to be directed. Because area per unit volume has a strong influence on the capillary pressure of a particular substrate, these high-surface-area fibers provide higher vertical wicking in that layer.

However, attempting to increase the capillarity of a secondary topsheet in these traditional ways may cause the secondary topsheet to become a stronger and a better competitor for the fluid, thus impairing transport of the fluid to lower, underlying layers of the absorbent core. As such, there remains a need for absorbent articles having improved absorption characteristics.

SUMMARY OF THE INVENTION

It has been discovered that the bridging problem of hydrophobic nonwoven or aperture film topsheets can also be addressed in a very different way. Providing trace amounts of superabsorbent material in intimate contact with the lower side of such a topsheet has been found to enable more efficient fluid bridging and improve the onset of fluid absorption through the topsheet, without significantly interfering with the subsequent transport of the fluid to the core.

Fibrous superabsorbent material has been found to be particularly useful for this purpose. This material may be immobilized within a fibrous matrix or placed in intimate contact with the topsheet in an airlaid layer that has a basis weight of less than about 125 grams per square meter. It may be preferred that the basis weight of such an airlaid layer be less than 100 grams per square meter, and most preferred that the basis weight of such a layer be less than 80 grams per square meter.

Within the web or airlaid layer, concentrations of between 0.30 and 3.5 grams of superabsorbent material per square meter are believed to be useful. It is preferred that the concentration be less than 2.5 grams per square meter, and most preferred that the concentration be less than 1.5 grams per square meter.

DETAILED DESCRIPTION OF THE INVENTION

The invention can be used in a variety of disposable absorbent articles, but is particularly useful in feminine hygiene products such as sanitary napkins and pantiliners. One embodiment of a disposable absorbent article that uses the invention is the sanitary napkin 10 shown in FIG. 1 and FIG. 2.

The illustrated sanitary napkin 10 has a body-facing upper side that contacts the user's body during use. The opposite, garment-facing lower side contacts the user's clothing during use.

Figure 1:
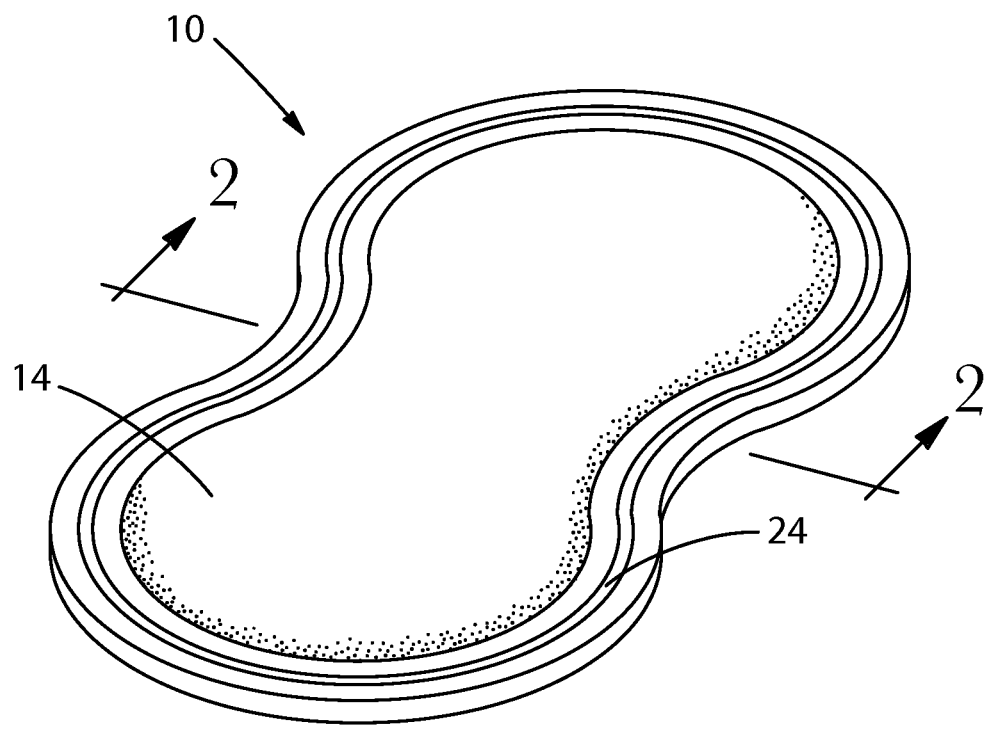
FIG. 1 is a perspective view of one embodiment of a sanitary napkin that uses the present invention.
Figure 2:
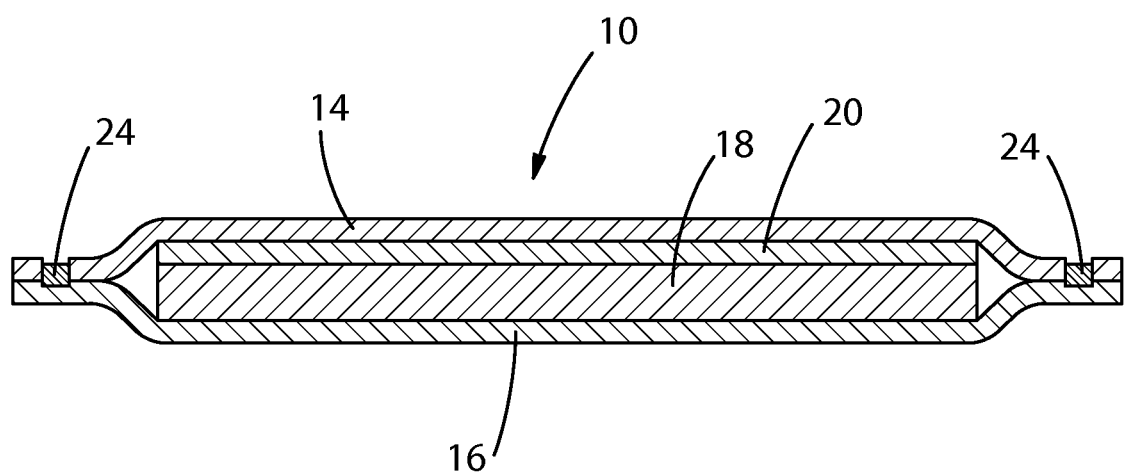
FIG. 2 is a cross-sectional view of the sanitary napkin of FIG. 1, taken through line 2-2.

A sanitary napkin 10 can have any shape known in the art for feminine hygiene articles, including the generally symmetric "hourglass" shape as shown in FIG. 1, as well as pear shapes, bicycle-seat shapes, trapezoidal shapes, wedge shapes or other shapes that have one end wider than the other. Sanitary napkins and pantiliners can also be provided with lateral extensions known in the art as "flaps" or "wings" (not shown in FIG. 1). Such extensions can serve a number of purposes, including, but not limited to, protecting the wearer's panties from soiling and keeping the sanitary napkin secured in place.

The upper side of a sanitary napkin generally has a liquid pervious topsheet 14. The lower side (seen in FIG. 2) generally has a liquid impervious backsheet 16 that is joined with the topsheet 14 at the edges of the product. An absorbent core 18 is positioned between the topsheet 14 and the backsheet 16. A secondary topsheet 20 may be provided at the top of the absorbent core 18, beneath the topsheet.

The topsheet 14, the backsheet 16, and the absorbent core 18 can be assembled in a variety of well-known configurations, including so called "tube" products or side flap products. Preferred sanitary napkin configurations are described generally in U.S. Pat. No. 4,950,264, "Thin, Flexible Sanitary Napkin" issued to Osborn on Aug. 21, 1990, U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, and "Shaped Sanitary Napkin With Flaps" issued to Van Tilburg on Aug. 18, 1987. Each of these patents is incorporated herein by reference.

The backsheet 16 and the topsheet 14 can be secured together in a variety of ways. Adhesives manufactured by H. B. Fuller Company of St. Paul, Minn. under the designation HL-1258 or H-2031 have been found to be satisfactory. Alternatively, the topsheet 14 and the backsheet 16 can be joined to each other by heat bonding, pressure bonding, ultrasonic bonding, dynamic mechanical bonding, or a crimp seal. A fluid impermeable crimp seal 24 can resist lateral migration ("wicking") of fluid through the edges of the product, inhibiting side soiling of the wearer's undergarments.

As is typical for sanitary napkins and the like, the sanitary napkin 10 of the present invention can have panty-fastening adhesive disposed on the garment-facing side of backsheet 16. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the wearer's panties.

For the purpose of describing the invention, the important parts of the sanitary napkin 10 are the topsheet 14, the absorbent core 18, and the secondary topsheet 20. Each of these components will be described in turn.

The Topsheet 14

To provide for softness next to the body, the topsheet 14 of the illustrated sanitary napkin 10 is formed from a soft, smooth, flexible, porous material that is non-irritating to the user's skin The topsheet 14 must be permeable to the body fluids to be collected by the article and thus, for a sanitary napkin, must be permeable to vaginal discharges.

Generally, topsheets for absorbent articles can be made from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Hydrophobic topsheets have a reduced tendency to allow fluids to pass back through and rewet the wearer's skin. Thus, the surface of the formed film (or nonwoven) that is in contact with the body remains dry, thereby reducing body soiling and creating a more comfortable feel for the wearer.

Preferred topsheets for use in the present invention are hydrophobic topsheets selected from typical nonwoven forming approaches such as spunbonded, carded, hydroentangled, needled, through-air bonded, or high loft nonwoven topsheets, and apertured 2-dimensional or 3-dimensional film topsheets. Lofty apertured formed film topsheets, with appreciable topsheet texture (nubs, micro-texture or with filament-like protrusions on the body-facing surface that can trap bodily discharges and hinder low fluid flows towards the body) that may be hydrophobic or hydrophilic in nature, can also be used. Apertured formed films are especially preferred for the topsheet 14 because they are pervious to body exudates and non-absorbent, Suitable formed film topsheets are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Other aperture-formed film topsheets are disclosed in U.S. Pat. No. 4,609,518 (Curro et al), issued Sep. 2, 1986 and U.S. Pat. No. 4,629,643 (Curro et al), issued Dec. 16, 1986, which are incorporated by reference. Other suitable topshetts are disclosed in, for example, U.S. Pat. Nos. 7,172,801; 7,270,861; 7,410,683; 7,507,459; 7,553,532; 7,648,752; 7,670,665; 7,682,686; 7,718,243; and U.S. Patent Appln. Nos. 2005/0281976; 2005/0283129; 2008/0119807; 2009/0030390; 2009/0030391. One useful topsheet for the present invention is the formed film described in one or more of the above patents and marketed on sanitary napkins sold by The Procter & Gamble Company of Cincinnati, Ohio as "DRI-WEAVE."

The Absorbent Core 18

The absorbent core 18 of a sanitary napkin serves to store bodily fluids discharged during use. The core 18 can be manufactured in a wide variety of sizes and shapes, and may be profiled to have different thickness, hydrophilic gradients, superabsorbent gradients, densities, or average basis weights at different positions across the face of the product.

An absorbent core 18 may have a fluid distribution layer as well as a fluid storage layer. The fluid distribution layer transfers received fluid both downwardly and laterally, and generally has more permeability and less capillarity than the fluid storage layer.

In addition to conventional absorbent materials such as creped cellulose wadding, fluffed cellulose fibers, wood pulp fibers also known as airfelt, and textile fibers, the fluid storage layer often includes superabsorbent material that imbide fluids and form hydrogels. These materials are typically capable of absorbing large quantities of body fluids and retaining them under moderate pressures. The fluid storage layer of the absorbent core 18 can be made solely of superabsorbent material, or can include such materials dispersed in a suitable carrier such as cellulose fibers in the form of fluff or stiffened fibers. Synthetic fibers including cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like can also be used. The fluid storage layer can also include filler materials, such as Perlite, diatomaceous earth, Vermiculite, or other suitable materials, that lower rewet problems.

However structured, the total absorbent capacity of the absorbent core 18 should be compatible with the design loading and the intended use of the article. Thus, the size and absorbent capacity of the absorbent core 18 may be varied to accommodate different uses such as incontinence pads, pantiliners, regular sanitary napkins, or overnight sanitary napkins.

The absorbent core 18 in the illustrated sanitary napkin is made of cellulose fibers and absorbent gelling material, such as, for example, described in International Patent Application Publication No. 00/59438 (Walker), herein incorporated by reference.

The absorbent core 18 can also include other optional components sometimes used in absorbent webs. For example, a reinforcing scrim can be positioned within the respective layers, or between the respective layers, of the absorbent core 18.

The backsheet 16 that covers the lower side of the absorbent core 18 prevents the fluids in the absorbent core 18 from wetting articles that contact the sanitary napkin 20, such as pants, pajamas and undergarments. Accordingly, the backsheet 16 is preferably made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

The Secondary Topsheet 20

The secondary topsheet 20 is interposed between the absorbent core 18 and the topsheet 14, and serves to rapidly draw discharged body fluids, in particular menstrual fluids, through the adjacent permeable (primary) topsheet 14. This allows the surface of the primary topsheet 14 adjacent the wearer of the article pad to remain relatively clean and dry.

It is desirable for the secondary topsheet 20 to have a basis weight of less than 125 grams per square meter, more preferred for it to have a basis weight of less than 100 grams per square meter, and most preferred for it to have a basis weight of less than 80 grams per square meter. The secondary topsheet 20 in the illustrated sanitary napkin 10 has a basis weight of 59 grams per square meter. It has a caliper thickness of 0.75 mm, a density of 0.08 grams/cubic centimeter, and a Permeability of 80 darcy.

Cellulosic Fibers

The secondary topsheet 20 in the illustrated sanitary napkin 10 has a fibrous web or matrix of hydrophilic cellulosic fibers, which contribute 34 grams per square meter to the basis weight of the secondary topsheet 20. This fibrous web or matrix provides the primary medium for handling aqueous fluids and in particular discharged aqueous body fluids. This web or matrix typically provides a capillary structure for handling such fluids. Such fluid handling includes acquiring the fluid through the topsheet 14 and distributing this fluid to the absorbent core 18. The web may store or fail to distribute small quantities quantities of the acquired liquid.

Many materials can be used to make this web or matrix, including both naturally occurring, unmodified cellulosic fibers such as cotton, Esparto grass, bagasse, kemp, flax, wood pulp, and jute, as well as modified cellulosic fibers such chemically modified wood pulp, rayon, and the like. Such fibers can be stiffened by chemical means.

The cellulosic fibers used in the illustrated secondary topsheet 20 are hydrophilic. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled Contact Angle, Wettability and Adhesion, edited by Robert F. Gould (Copyright 1964). A fiber, or surface of a fiber, is said to be wetted by a fluid (i.e., hydrophilic) when either the contact angle between the fluid and the fiber, or its surface, is less than 90 degrees, or when the fluid tends to spread spontaneously across the surface of the fiber, both conditions normally co-existing. Conversely, a fiber or surface is considered to be hydrophobic if the contact angle is greater than 90 degrees and the fluid does not spread spontaneously across the surface of the fiber.

Thermoplastic Material

The structure of hydrophilic cellulosic fibers in the illustrated secondary topsheet 20 can be solidified by thermoplastic material. Upon melting, at least a portion of this thermoplastic material migrates to the intersections of the fibers which become bond sites for the thermoplastic material. When cooled, the thermoplastic material at these intersections solidify to form the bond sites that hold the web or matrix of fibers.

Thermoplastic particulates or fibers can be used for this purpose. The materials, and in particular thermoplastic fibers, can be made from a variety of thermoplastic polymers including polyolefins such as polyethylene (e.g., PULPEX®) and polypropylene, polyesters, copolyesters, and copolymers of any of the foregoing.

Depending upon the desired characteristics for the resulting thermally bonded matrix, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, the term "bicomponent fibers" refers to thermoplastic fibers that comprise a core fiber made-from one polymer that is encased within a thermoplastic sheath made from a different polymer. The polymer comprising the sheath often melts at a different, typically lower, temperature than the polymer comprising the core 18. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

The length of bicomponent fibers can vary depending upon the particular properties desired for the fibers and the web formation process. Typically, in an airlaid web, these thermoplastic fibers have a length from about 2 mm to about 12 mm long, preferably from about 2.5 mm to about 7.5 mm long, and most preferably from about 3.0 mm to about 6.0 mm long. The properties-of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine can have a decitex in the range from about 1.0 to about 20, preferably from about 1.4 to about 10, and most preferably from about 1.7 to about 7 decitex.

In the illustrated secondary topsheet 20, 3 mm long bicomponent synthetic fibers with a decitex of 2.2 are used, contributing 0.6 grams per square meter to the basis weight of the secondary topsheet 20. These fibers can be purchased from Trevira GmbH of Germany as Trevira Type HC255-B BiCo fibers.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective thermally bonded fibrous matrix.

The secondary topsheet 20 in the illustrated sanitary napkin can also include synthetic fibers that typically do not function as binder fibers but alter the mechanical properties of the fibrous webs. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, preferably from about 0.9 to about 1.5 cm. Suitable nonbonding thermoplastic fibers can have a decitex in the range of about 1.5 to about 35 decitex, more preferably from about 14 to about 20 decitex.

Superabsorbent Material

Suitable absorbent gelling materials for use in the invention will most often comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 (Brandt et al), issued Mar. 31, 1987, and reissued as RE 32,649 on Apr. 19, 1988, both of which are incorporated by reference. Preferred monomers include acrylic acid, methacrylic acid, and 2-acrylamido-2-methyl propane sulfonic acid. Acrylic acid itself is especially preferred for preparation of the polymeric gelling material. The polymeric component formed from the unsaturated, acid-containing monomers can be grafted onto other types of polymer moieties such as starch or cellulose. Polyacrylate grafted starch materials of this type are especially preferred. Preferred polymeric absorbent gelling materials that can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric absorbent gelling materials, such materials will in general be slightly crosslinked. Crosslinking serves to render the hydrogel-forming polymer gelling materials substantially water-insoluble, and crosslinking thus in part determines the gel volume and extractable polymer characteristics of the hydrogels formed from these polymeric gelling materials. Suitable crosslinking agents are well known in the art and include, for example, those described in greater detail in U.S. Pat. No. 4,076,663 (Masuda et al); issued Feb. 28, 1978, which is incorporated by reference. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole percent to 5 mole percent of the resulting hydrogel-forming polymer material. More preferably, the crosslinking agent will constitute from about 0.01 mole percent to 3 mole percent of the hydrogel-forming polymeric gelling material.

The slightly crosslinked, hydrogel-forming polymeric gelling materials are generally employed in their partially neutralized form. For purposes of the present invention, such materials are considered partially neutralized when at least 25 mole per-cent, and preferably at least 50 mole percent of monomers used to form the polymer are acid group-containing monomers that have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

While these absorbent gelling materials are typically in particle form, it is also contemplated that the absorbent gelling material can be in the form of macrostructures such as fibers, sheets or strips. These macrostructures are typically prepared by forming the particulate absorbent gelling material into an aggregate, treating the aggregated material with a suitable crosslinking agent, compacting the treated aggregate to densify it and form a coherent mass, and then curing the compacted aggregate to cause the crosslinking agent to react with the particulate absorbent gelling material to form a composite, porous absorbent macrostructure. Such porous, absorbent macrostructures are disclosed, for example, in U.S. Pat. No. 5,102,597 (Roe et al), issued Apr. 7, 1992, which is incorporated by reference.

In the secondary topsheet 20 used in the disclosed sanitary napkin 10, fibrous superabsorbent material is used. The material is 6 mm long with a decitex of 10. Suitable material can be purchased from Technical Absorbents of the United Kingdom as Oasis type 111.

In certain embodiments, it is preferred to use a trace amount or less than about 3.5 grams per square meter of superabsorbent material, such as, for example, between 0.3 and 3.5 grams per square meter of superabsorbent material, more preferred to use between 0.3 and 2.5 grams per square meter of such material, and most preferred to use between 0.3 and 1.5 grams per square meter of such material. The superabsorbent material may be placed in intimate contact with the lower side of the topsheet 14. In the secondary topsheet 20 used in the illustrated sanitary napkin, the fibrous superabsorbent material contributes 0.6 grams per square meter to the basis weight of the secondary topsheet 20.

Formation of the Secondary Topsheet

The mixtures of fibers, thermoplastic material, and superabsorbent material can be formed into layers by any of a variety of techniques, including wet-laying methods and air-laying methods. Techniques for wet-laying cellulosic fibrous material to form paper are well known in the art.

More typically, the secondary topsheet 20 can be by air-laying the mixture of fibers and thermoplastic material. In general, air-laying can be carried out by metering an airflow containing the fibers and thermoplastic material, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al), issued Oct. 5, 1982; U.S. Pat. No. 4,353,687 (Hosler et al), issued Oct. 12, 1982; U.S. Pat. No. 4,494,278 (Kroyer et al), issued Jan. 22, 1985; U.S. Pat. No. 4,627,806 (Johnson), issued Dec. 9, 1986; U.S. Pat. No. 4,650,409 (Nistri et al), issued Mar. 17, 1987; and U.S. Pat. No. 4,724,980 (Farley), issued Feb. 16, 1988, all of which are incorporated by reference.

A particularly desirable system for air-laying mixtures of fibers and thermoplastic material according to the present invention is disclosed in U.S. Pat. No. 4,640,810 (Laursen et al), issued Feb. 3, 1987, which is incorporated by reference.

The secondary topsheet 20 in the illustrated sanitary napkin 10 is formed by airlaying the cellulose, thermoplastic material, and fibrous superabsorbent material onto a nonwoven carrier made of spunbonded polypropylene. This nonwoven carrier contributes 10 grams per square meter to the basis weight of the secondary topsheet 20. The fibrous superabsorbent material is added into the second of three active forming heads causing it to lie near the middle of the absorbent airlaid web. This ensures that the fibrous superabsorbent material is physically contained within a fibrous matrix and allows the absorbent airlaid web to be oriented with either the top or bottom surface facing towards the topsheet 14. 2.5 grams per square meter of latex are sprayed onto both sides of the resultant material.

There are different ways to combine the secondary topsheet 20 and the absorbent core 18. The secondary topsheet 20 can be formed separately from the absorbent core 18 and then combined later after thermal bonding/densification. Alternatively, the secondary topsheet 20 and all or parts of the absorbent core can be formed on top of the other.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable article that has:
    a hydrophobic nonwoven or film topsheet;
    an absorbent core; and
    a secondary topsheet that a) is positioned between the absorbent core and the topsheet, b) has a basis weight of 40-80 grams per square meter of surface area, and c) contains a mixture of cellulose, bi-component fiber, and between 0.30 and 1.5 grams per square meter of fibrous superabsorbent material air-laid onto a non-woven carrier;
    wherein the secondary topsheet further comprises a latex coating sprayed onto both sides of the secondary topsheet.

2. A disposable article as recited in claim 1, in which the disposable absorbent article is selected from the group consisting of sanitary napkins and pantiliners.

3. The disposable article as recited in claim 1, wherein the non-woven carrier has a basis of weight of 10 grams per square meter or less.

* * * * *